(12) United States Patent
Karapetyan

(10) Patent No.: US 7,144,251 B1
(45) Date of Patent: Dec. 5, 2006

(54) DENTAL-FACIAL MEASURING INSTRUMENT

(76) Inventor: Armen Karapetyan, 1935 N. Van Ness Ave., Los Angeles, CA (US) 90068

( * ) Notice: Subject to any disclaimer, the term of this patent is extended or adjusted under 35 U.S.C. 154(b) by 101 days.

(21) Appl. No.: 10/989,676

(22) Filed: Nov. 16, 2004

(51) Int. Cl.
*A61C 19/04* (2006.01)

(52) U.S. Cl. .............. 433/72; 433/73; 433/75; 33/513

(58) Field of Classification Search ............ 433/72, 433/68, 69, 73, 75; 33/513
See application file for complete search history.

(56) References Cited

U.S. PATENT DOCUMENTS

| | | | | |
|---|---|---|---|---|
| 2,154,148 A | * | 4/1939 | Butts | 33/513 |
| 2,540,555 A | * | 2/1951 | Slaughter, Jr. | 33/513 |
| 4,028,810 A | * | 6/1977 | Vice | 433/75 |
| 4,261,696 A | * | 4/1981 | Hobo | 433/73 |
| 4,718,850 A | | 1/1988 | Knebelman | |
| 4,843,720 A | * | 7/1989 | Kim | 33/812 |
| 5,971,756 A | * | 10/1999 | Fjelstad | 433/68 |
| 6,582,931 B1 | | 6/2003 | Kois et al. | |

* cited by examiner

*Primary Examiner*—Melba N. Bumgarner
*Assistant Examiner*—Jonathan Werner

(57) ABSTRACT

A dental-facial measuring instrument provides a possibility to determine an occlusion to make a denture. An improved dental-facial measuring instrument includes the first and second strips coupled by the connector and spring with a slidable strip comprising a horizontal portion and a scale, and wherein the first and second corbels of the slidable strip are appropriately inserted into the first and second slots of the first strip and second strip respectively.

1 Claim, 3 Drawing Sheets

DENTAL-FACIAL MEASURING INSTRUMENT

FIELD OF THE INVENTION

The present invention relates to dental instrument, and more particularly to a dental system for transferring dental-facial information from a patient to a dental articulator to facilitate accurate mounting of dental study casts on the articulator for the diagnosis and treatment of both aesthetics and function, e.g. for measuring certain vertical dimensions on the human face for use in making dentures, but the instrument is not limited to any particular use.

BACKGROUND OF THE INVENTION

The accurate determination of the vertical jaw relation is extremely important in the fitting of dentures, as well as in other dental restoration work.

Two long-standing and troublesome problems in making dentures are obtaining the proper occlusion or bite between the upper or lower dentures and to determine the width of the teeth. The fit, appearance and the functional operation of dentures are extremely important, and have long been quite difficult to accomplish.

In analyzing and treating jaw disorders and in making dental prostheses, it is desirable to simulate the patient's jaw movements. To do this on a dental articulator, it is first necessary to analyze the jaw movements and then transfer the information to a dental articulator to enable the articulator to move in a manner to simulate the patient's jaw movements. This enables the dentist or technician to test and shape dental prostheses on the articulator before mounting them in the patient's mouth.

Vertical dimension of occlusion, i.e. the vertical dimension of the face with the posterior teeth fitting tightly together, is readily determined by a method comprising first measuring the distance between the external auditory meatus and the lateral corner of the ocular orbit, making an adjustment in the first measurement to arrive at the factored distance and then positioning the mandible so that the distance between the nasal spine and the anterior part of the undersurface of the mandible corresponds to the factored distance.

The accurate determination of the vertical jaw relation is extremely important in the fitting of dentures, as well as in other dental restoration work. Vertical relation, or vertical dimension refers to the degree of separation between the mandible, or lower jaw-bone and the maxillae, or upper jaw-bone. An appreciable increase or decrease in the vertical dimension of the mandible to the maxillae may cause problems in masticatory performance and speech. Deviations in vertical dimension may also cause temporomandibular joint disorders, which are often accompanied by severe physical discomfort in the jaw and neck regions. In certain cases, soreness of the supporting tissues may result, making the jaw region a target for rapid bone resorption.

In practice, the determination of the occlusal vertical dimension is the starting point for complete denture treatment. Occlusal vertical dimension is generally defined as the vertical dimension of the face when the teeth are in natural maximum contact in centric occlusion, i.e., with the posterior teeth fitting tightly together. Determination of the occlusal vertical dimension establishes the reference position from which all other horizontal jaw relation positions are recorded.

Many techniques have been proposed heretofore for facilitating the determination of occlusal vertical dimension. Preextraction records, such as profile photographs, softwire profile silhouettes, occluded diagnostic casts, resin face masks and facial measurements have been found to be of value in many cases. Various instruments have been used for making facial measurements, including Sorenson's profile guide and the Willis device. More sophisticated approaches, such as radiographic techniques and electromyography have also been used. The Boos Bimeter, a device that measures the maximum force of jaw closure has been advocated by some clinicians and researchers. In addition, the patient's swallowing threshold, closest speaking space, phonetics, tactile sense, and parallelism of the ridges in the posterior region of the jaw have been used with varying degrees of success.

Although there are a number of different approaches in use, it is generally acknowledged by experienced prosthodontist that there is no precise scientific method of determining the correct occlusal vertical dimension. The acceptability of any vertical dimension determination depends largely upon the skill, experience and judgment of the prosthodontist. Thus, a need exists for a reliable method for accurately determining vertical dimension to facilitate dental restorations.

There are a variety of the instruments described in the patents for obtaining information about the jaw vertical positions and movements, all of which have various complexities and disadvantages.

For example, in the dento-facial analyzer disclosed by U.S. Pat. No. 6,582,931, the height of the lip commisures can be measured up from the index tray and marked on the dental cast to help evaluate the height of the teeth to enhance the person's smile to the curvature of the lips. Further, the vertical indicator rod is utilized and analyzed for best considering the length of the incisor or vertical dimension of occlusion in relation to other facial proportions. The mounting platform can be adjusted vertically in millimeters to a desired incisor length. That is, with the dental cast supported by the upper frame of the articulator and the incisal pin, and the platform lowered a desired amount, the length of the incisors could be increased to be aligned with the incisal line on the platform.

While this known instrument is relatively accurate, it is unfortunately still somewhat complicated and time consuming, requiring many different steps, comprising many components including screws to tighten and the bite fork need to be sterilized before each use. Also, such device is an expensive construction.

The gauging device described in U.S. Pat. No. 4,718,850 includes a first probe terminating in a first tip portion affording registry thereof with the above-noted anatomical features or parts and a second probe which is adjustably mounted substantially parallel to the first probe for adjustment relative to the first probe and which has a second tip portion affording registry of complementary anatomical features or parts therewith. In practicing the method of the invention, one of the tips of the gauging device is placed in registry with the external auditory meatus and the device is then adjusted to register the other of the tips with the lateral corner of the ocular orbit to establish an initial measurement. The tip of the second probe is then positioned a factored distance relative to the tip of the first probe, based on the first measurement. Thereafter, and without changing the relative positions of the tips of the gauging device, one of the tips is placed in registry with the nasal spine and the other tip is positioned adjacent the anterior part of the undersurface of the mandible and the mandible is then positioned to engage the other tip. The gauging device is provided with a scale to facilitate making the initial measurement and positioning the second probe to account for the factored distance. The tips of the probes have to be strictly paralleled each to other. More specifically, the device comprises an elongated rod-like body having an elongated axis, with first probe adjacent one end of the body projecting transversely from the axis and a slide axially adjustable on the rod-like body. The second probe is disposed on and projects from the slide substantially parallel to the first probe. A scale is provided longitudinally on the rod-like body, which lies along the path of adjustment of the slide. Each probe has a tip portion adopted for registry with selected anatomical parts, including the external auditory meatus, the lateral corner of the ocular orbit, the nasal spine and the most anterior part of the sub-mental region of the mandible. The scale facilitates the initial measurement and positioning of the second probe in arriving at the final measurement, after accounting for the factored distance. The scale may be provided on the exterior of the rod-like body during the forming operation, or thereafter, by techniques such as engraving or etching. Also, the gauging device may include a stop means for maintaining the relative position of the probes at any desired spacing on the rod-like body. To this end, the gauging device is provided with a set screw, which passes through the sleeve and frictionally engages the rod-like body. The rod-like body of the gauging device is formed with a longitudinal groove or slot, in which the tip of the set screw rests, in order to maintain the first and second probes in substantially parallel relationship. Additionally, the scale has a single set of indicia calibrated to establish the actual distance between the probe tips. Alternatively, the scale has dual sets of indicia, one of which establishes the initial measurement of the procedure and the other of which is correlated to the first set to establish the factored distance corresponding to the initial measurement on the first set of indicia. Another concept of the device is a forceps-like or scissor-type gauging device. In this case the device comprises a pair of arms, journalled on suitable pin means intermediate their ends to allow displacement of the arms relative to one another about a pivotal axis concentric with the pin means. The first probe is articulated adjacent one end of one arm of the pair of arms and the second probe is articulated on the corresponding end of the other arm of the pair of arms, the arm ends on which the probes are mounted being disposed on the same side of the pivotal axis, with the tips of the probes being parallel to one another. An arcuate scale is provided which is centered on the pivotal axis. The scale may be rigidly affixed to one of the arms, as shown, with the scale making frictional contact along its length with the other arm, in order to maintain any desired spacing between probes. The pin means may be designed so that a threshold applied force must be exceeded before the arms may be displaced with respect to one another. The vertical dimension determining of occlusion process requires the tabling of the measured results and accounting for the factored distance.

This known device is relatively accurate, it is unfortunately still complicated, requiring some calculations ("accounting for the factored distance") and comprising many components including screws to tighten. Also, such device is an expensive construction and does not provide visual perception of the occlusion.

Another dental measuring instrument by U.S. Pat. No. 4,843,720 is also intended to measure the vertical distance from the underside of the chin to the underside of the nose, for use in making dentures. This device comprises the two gauge blocks having non-confronting face engaging surfaces at the opposite side of the measuring strip. When the measuring strip is vertically positioned in front of the face, a horizontal top edge surface on the fixed block engages the underside of the nose, and a horizontal surface on the movable block engages the underside of the chin. Fixedly mounted on one end of a flat measuring strip is a gauge block projecting on opposite sides of the measuring strip. An elongated transverse measuring block is slidably mounted on measuring strip with the ends of the block projecting from opposite sides of the measuring strip in the plane of the fixed block. The back face of block has a resilient tongue with a lug normally pressing against a smooth back face surface of the measuring strip to prevent free sliding of block on the measuring strip. The free end of tongue has a push button projection which projects forward through an opening in the front face of block, whereby depressing the push button disengages lug from the measuring strip to allow free sliding movement of block on the measuring strip.

This device still comprises the controllable components which are used for the tightening purposes e.g. the controllable button projection used for the tightening purposes). Also, such device does not provide visual perception of the occlusion.

Thus, there is a great need in the art for the improved not complex and not expensive dental-facial measuring instrument for dental articulation accuracy providing measurement authenticity and visual perception of the occlusion without any additional calculations/accounting.

OBJECT AND ADVANTAGES OF THE INVENTION

Accordingly, several objects and advantages of the present invention are to provide convenient and effective dental-facial measuring instrument.

It is another object of the invention to eliminate necessity of the hand-tightening components.

It is still another object of the invention to reduce the time of the dental-facial measuring.

Still, further objects and advantages will become apparent from a consideration of the ensuing description accompanying drawings.

DESCRIPTION OF THE DRAWING

In order that the invention and the manner in which it is to be performed may be more clearly understood, embodiments thereof will be described by way of example with reference to the attached drawings, of which.

SUMMARY OF THE INVENTION

A dental-facial measuring instrument provides a possibility to determine an occlusion to make a denture.

An improved dental-facial measuring instrument includes the first and second strips coupled by the connector and spring with a slidable strip comprising a horizontal portion and a scale, and wherein the For the dental-facial measuring, the instrument is vertically positioned in front of the face, an upper surface of the horizontal portion engages the underside of the nose, and at first measurement a horizontal surface of the second strip engages the underside of the chin and at second measurement a horizontal surface of the first strip engages the underside of the chin.

DESCRIPTION OF THE PREFERRED EMBODIMENTS

Herein the description of an improved dental-facial measuring instrument (device) will be done in statics (as if the components of the improved device are suspended in the space) with description of their relative connections to each other. The description of the functional operations of an improved device will be done hereinafter.

Figure 1:
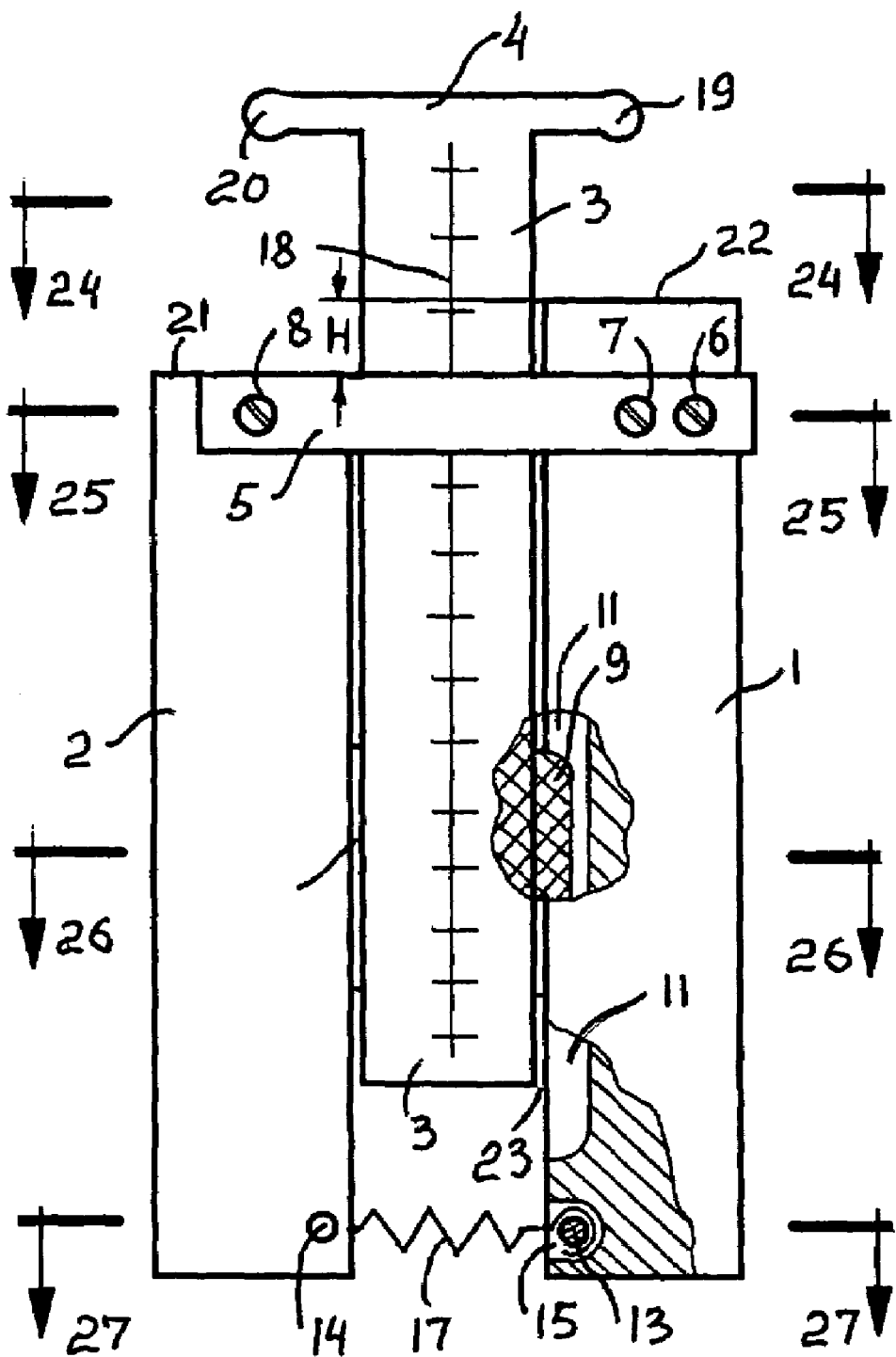
FIG. 1 is a simplified drawing of the improved dental-facial measuring instrument.
Figure 2:
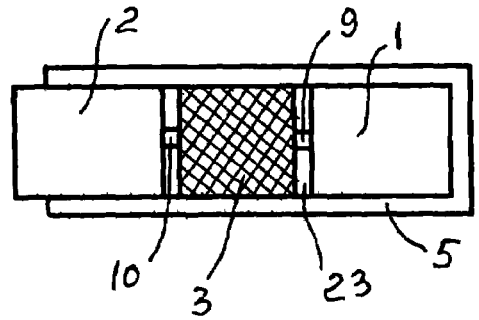
FIG. 2 is a simplified cross-sectional view 24—24.
Figure 3:
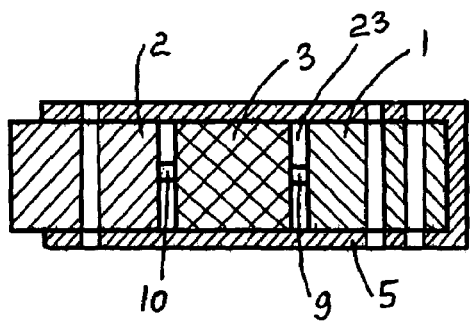
FIG. 3 is a simplified cross-sectional view 25—25.
Figure 4:
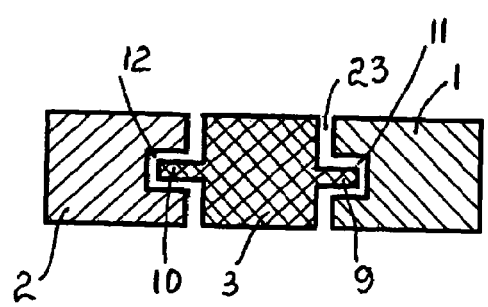
FIG. 4 is a simplified cross-sectional view 26—26.
Figure 5:
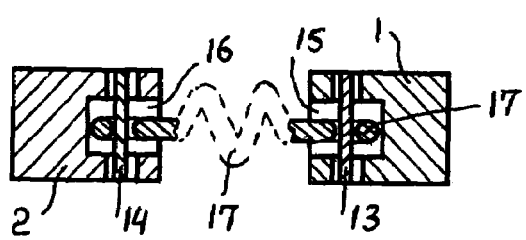
FIG. 5 is a simplified cross-sectional view 27—27.

An improved dental-facial measuring instrument, referring to FIG. 1, includes a first strip 1 comprising a first slot 11, a second strip 2 including a second slot 12 (see also FIGS. 2–4), a slidable (movable) strip 3 comprising a first corbel 9 and a second corbel 10 as shown in FIGS. 1–4, a horizontal portion 4 including a first safety edge 19 and a second safety edge 20, a connector 5, a first screw 6, a second screw 7, a third screw 8, a first pin 13, a second pin 14, a first opening 15 (see FIGS. 1, 5), a second opening 16 as shown in FIG. 5, a spring 17, a scale 18, a first horizontal surface 21 and a second horizontal surface 22. The corbels 9 and 10 are slidable in the slots 11 and 12 respectively. The connector 5 is by the first screw 6 and second screw 7 coupled with the first strip 1, and by third screw 8 is coupled with the second strip 2. The connector 5 can be of any geometrical configuration and form, and can be attached to the strips by any reasonable means, e.g. by a rivets (not shown), pins (not shown), etc. or, for instance, can glued (not shown) to the first 1 and second 2 strips.

Referring to FIG. 5 with regards to FIG. 1, the ends of the spring 17 are appropriately inserted into first opening 15 and second opening 16, and fixed by the pins 13 and 14 respectively. The fixation of the spring's ends in the openings 15 and 16 can be provided by any reasonable means, e.g. such as screws (not shown), rivets (not shown), etc. The horizontal portion 4 can be provided with the first safety edge 19 and second safety edge 20 to prevent the face of the injury (e.g. face scratches, etc.). The horizontal portion 4 can be attached to the slidable strip 3 or the slidable strip 3 and horizontal portion 4 can be made of a solid piece of material. The scale 18 can be presented in metric or inch system (in FIG. 1 the scale is shown conditionally without any digits). Also, the scale 18 can include more scale's marks and may be wider or can be located not in the center of the slidable strip 3, as it is shown in FIG. 1.

Figure 6:
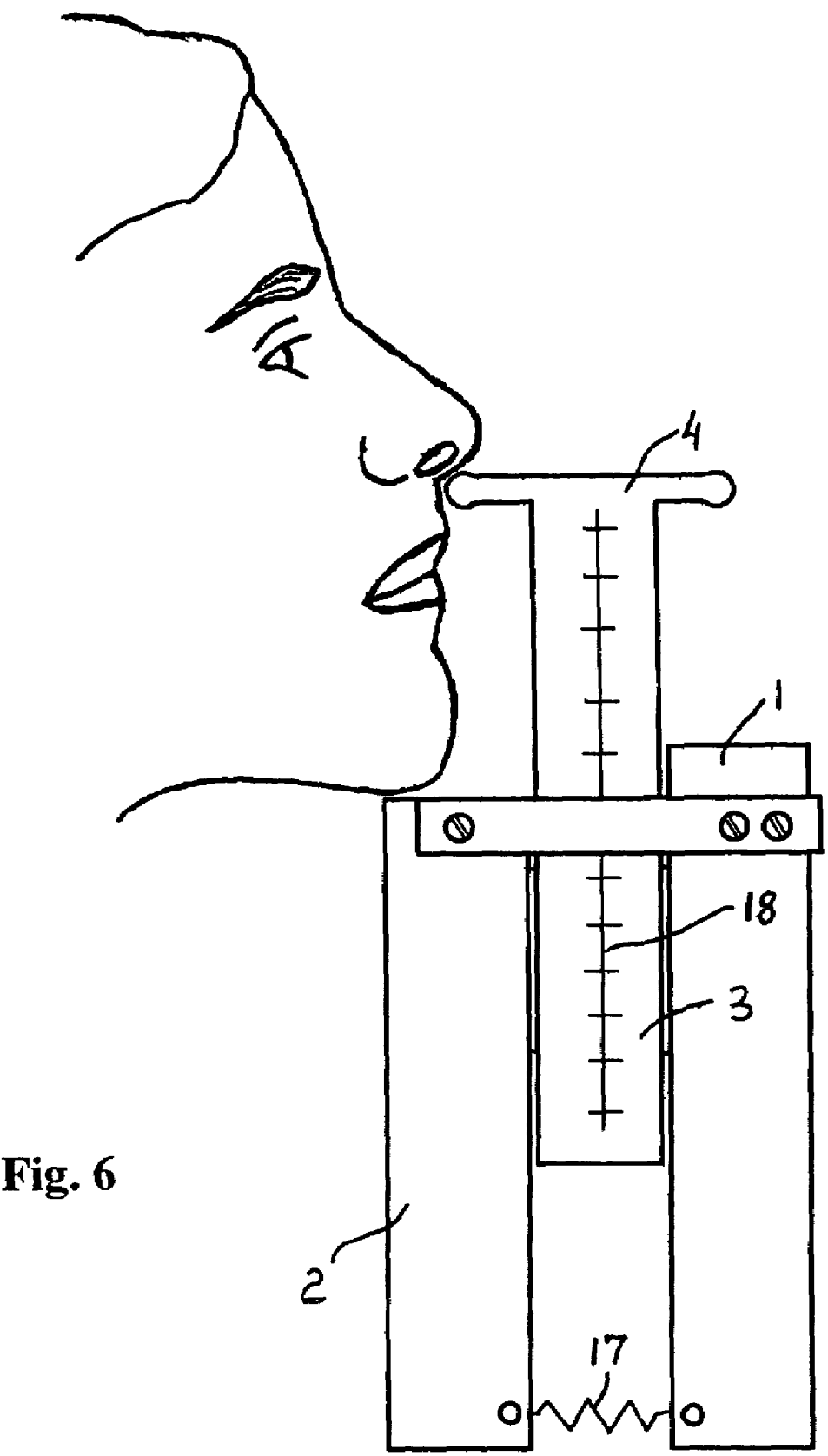
FIG. 6 is a simplified illustration of the dental-facial measuring process (how the instrument is applied to the face to provide the measurements).

The vertical dimension of occlusion can be readily determined as the distance between the nasal spine and the anterior part of the undersurface of the mandible. According to FIG. 6, the operator (e.g. dentist or dental technician, etc.) positions the instrument in front of the face than measures the vertical distance from the underside of the chin to the underside of the nose, for use in making dentures. More specifically, the operator, at first, by the second strip 2 (jaw's physically normal position [no occlusion/no jaw's bite position/]) measures the distance between the upper surface of the horizontal portion 4 and second horizontal surface 22, and the second measurement is provided by the first strip 1 and slidable strip 3 determining the distance between the upper surface of the horizontal portion 4 and first horizontal surface 21 ([occlusion/jaw's bite position). The distance "H" is varied from individual to individual and commonly may be in the range of about 2–3 mm. The spring 17 provides-tightening (not shown) of the lower part of the slidable strip 3 with the lower parts of the first strip 1 and second strip 2, thereby eliminating the gaps 23 and squeezing the strip 3 between strips 1 and 2.

The strips 1–3 and/or connector 5 can be preferably made of any reasonable material, for example, such as relatively hard plastic material, (e.g. acrylic resin, polyvinyl chloride [PVC] or polyamide polymer, which can be formed into the desired shape by conventional molding or casting operations). If desired, the device may also be made out of metal, (e.g. such as aluminum or stainless steel, by a suitable metal forming operation, e.g. casting or machining) or wood. In either case, the material selected should be one that can withstand repeated measuring processes, and in some cases be withstandable for the repeated sterilization procedures. All components and means of the improved dental-facial measuring instrument can be of any reasonable color, size, form and/or configuration.

Thus, an improved dental-facial measuring instrument provides convenient, effective and non-expensive device to define the occlusion for use in making dentures.

CONCLUSION, RAMIFICATION AND SCOPE

Accordingly the reader will see that, according to the invention, I have provided a dental-facial measuring instrument, providing convenient, effective not complex and not expensive dental-facial measuring instrument for dental articulation accuracy providing measurement authenticity and visual perception of the occlusion. An improved dental-facial measuring instrument has various possibilities, considering activities of the dental practice.

While the above description contains many specificities, these should be not construed as limitations on the scope of the invention, but as exemplification of the presently-preferred embodiments thereof. Many other ramifications are possible within the teaching to the invention. For example, an improved dental-facial measuring instrument eliminates the necessity of the dentist's staff (technicians) to make any calculation (accounting) and/or tables to determine the occlusion.

Thus, the scope of the invention should be determined by the appended claims and their legal equivalents, and not by examples given.

THE DRAWING REFERENCE NUMERALS WORKSHEET

1.—a first strip;
2.—a second strip;
3.—a slidable strip;
4.—a horizontal portion;
5.—a connector;
6.—a first screw;
7.—a second screw;
8.—a third screw;
9.—a firs corbel;
10.—a second corbel;
11.—a first slot;
12.—a second slot;
13.—a first pin;

14.—a second pin;
15.—a first opening;
16.—a second opening;
17.—a spring;
18.—a scale;
19.—a first safety edge;
20.—a second safety edge;
21.—a first horizontal surface;
22.—a second horizontal surface;
23.—a gap;
24—24—a cross-sectional view;
25—25—a cross-sectional view;
26—26—a cross-sectional view;
27—27—a cross-sectional view.

What is claimed is:

1. A dental-facial measuring instrument comprising a first strip of vertically elongated configuration including a first horizontal surface and a first slot located into left side of said first strip;

a second strip of vertically elongated configuration including a second horizontal surface and a second slot located into right side of said first strip, and wherein said second horizontal surface is lower than said first horizontal surface;

a slidable strip of vertically elongated configuration including a scale, a first corbel located on one side of said slidable strip, a second corbel located on another side of said slidable strip, and a horizontal portion comprising a first safety edge and a second safety edge, and wherein said slidable strip is located between said first strip and said second strip, and wherein said first corbel is inserted into said first slot and said second corbel is inserted into said second slot;

a connector coupling said first strip with said second strip at their upper portion, and wherein said coupling of said first strip with said second strip by said connector provides a sliding of said slidable strip between said first strip and said second strip;

a spring coupling said first strip and said second strip at their lower portion, and wherein the ends of said spring are appropriately inserted into a first opening of said first strip and into a second opening of said second strip, and appropriately attached to said first strip and to said second strip.

* * * * *